United States Patent
Tevs

(10) Patent No.: US 9,395,171 B2
(45) Date of Patent: Jul. 19, 2016

(54) CAPACITIVE SENSOR WITH ORTHOGONAL FIELDS

(71) Applicant: Nikolai R. Tevs, Daytona Beach Shores, FL (US)

(72) Inventor: Nikolai R. Tevs, Daytona Beach Shores, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 601 days.

(21) Appl. No.: 13/668,345

(22) Filed: Nov. 5, 2012

(65) Prior Publication Data

US 2014/0125361 A1    May 8, 2014

(51) Int. Cl.
| | |
|---|---|
| G01R 27/26 | (2006.01) |
| G01B 7/02 | (2006.01) |
| G01D 5/24 | (2006.01) |
| H01L 21/00 | (2006.01) |

(52) U.S. Cl.
CPC .............. *G01B 7/023* (2013.01); *G01D 5/2405* (2013.01); *C12Q 2326/00* (2013.01); *H01L 21/00* (2013.01); *H01L 2221/00* (2013.01)

(58) Field of Classification Search
CPC . H01L 21/00; H01L 2221/00; H01L 2924/00; H01L 2925/00; C12Q 1/00; C12Q 2326/00
USPC ......... 324/458, 679, 609, 658, 661, 663, 665, 324/672, 686, 693, 695, 705, 162, 161, 163, 324/165, 176, 76.74, 76.78
See application file for complete search history.

(56) References Cited

U.S. PATENT DOCUMENTS

| | | | |
|---|---|---|---|
| 4,255,976 A * | 3/1981 | Formato ..................... 73/861.08 | |
| 4,395,827 A | 8/1983 | Stowe et al. | |
| 4,419,044 A | 12/1983 | Barry et al. | |
| 4,876,505 A | 10/1989 | Osborne | |
| 5,287,630 A * | 2/1994 | Geisler ............... G01D 5/2497 | 33/706 |
| 5,649,369 A | 7/1997 | Thoren | |
| 5,801,340 A * | 9/1998 | Peter ...................... G01S 13/04 | 178/20.04 |
| 7,270,890 B2 | 9/2007 | Sabol et al. | |
| 7,572,524 B2 | 8/2009 | Sabol et al. | |
| 7,582,359 B2 | 9/2009 | Sabol et al. | |
| 7,618,712 B2 | 11/2009 | Sabol et al. | |
| 7,836,772 B2 | 11/2010 | Twerdochlib | |
| 8,076,948 B2 * | 12/2011 | Knoedgen et al. ............ 324/658 |
| 8,363,031 B2 * | 1/2013 | Geaghan ....................... 345/174 |
| 2003/0047456 A1 * | 3/2003 | Medoro ........................ 204/547 |
| 2005/0104596 A1 * | 5/2005 | Fleury ........................... 324/376 |
| 2007/0008299 A1 * | 1/2007 | Hristov ................. G06F 3/0416 | 345/173 |

(Continued)

OTHER PUBLICATIONS

TURBOCOAX; High temperature Capacitive Sensors; THERMOCOAX from vision to reality.

*Primary Examiner* — Huy Q Phan
*Assistant Examiner* — Temilade Rhodes-Vivour

(57) ABSTRACT

A method and system for determining a distance from a probe to an object includes generating a first electric field by applying a first signal across a first pair of electrodes aligned along a first axis and generating a second electric field by applying a second signal across a second pair of electrodes aligned along a second axis substantially perpendicular to the first axis. After generating the signals, a first change in the first signal due to the object interacting with the first electric field and a second change in the second signal due to the object interacting with the second electric field is concurrently detected. A distance of the object from the first and second pair of electrodes can be calculated based on a ratio of the first and second changes.

20 Claims, 6 Drawing Sheets

(56) References Cited

U.S. PATENT DOCUMENTS

| | | | |
|---|---|---|---|
| 2007/0062739 A1* | 3/2007 | Philipp | G06F 3/044 178/18.06 |
| 2007/0227255 A1* | 10/2007 | Goldfine et al. | 73/779 |
| 2009/0289620 A1 | 11/2009 | Suckling et al. | |
| 2012/0169635 A1* | 7/2012 | Liu | G06F 3/0412 345/173 |
| 2012/0269478 A1* | 10/2012 | Anderson et al. | 385/3 |
| 2013/0147833 A1* | 6/2013 | Aubauer | G06F 3/0416 345/619 |

* cited by examiner

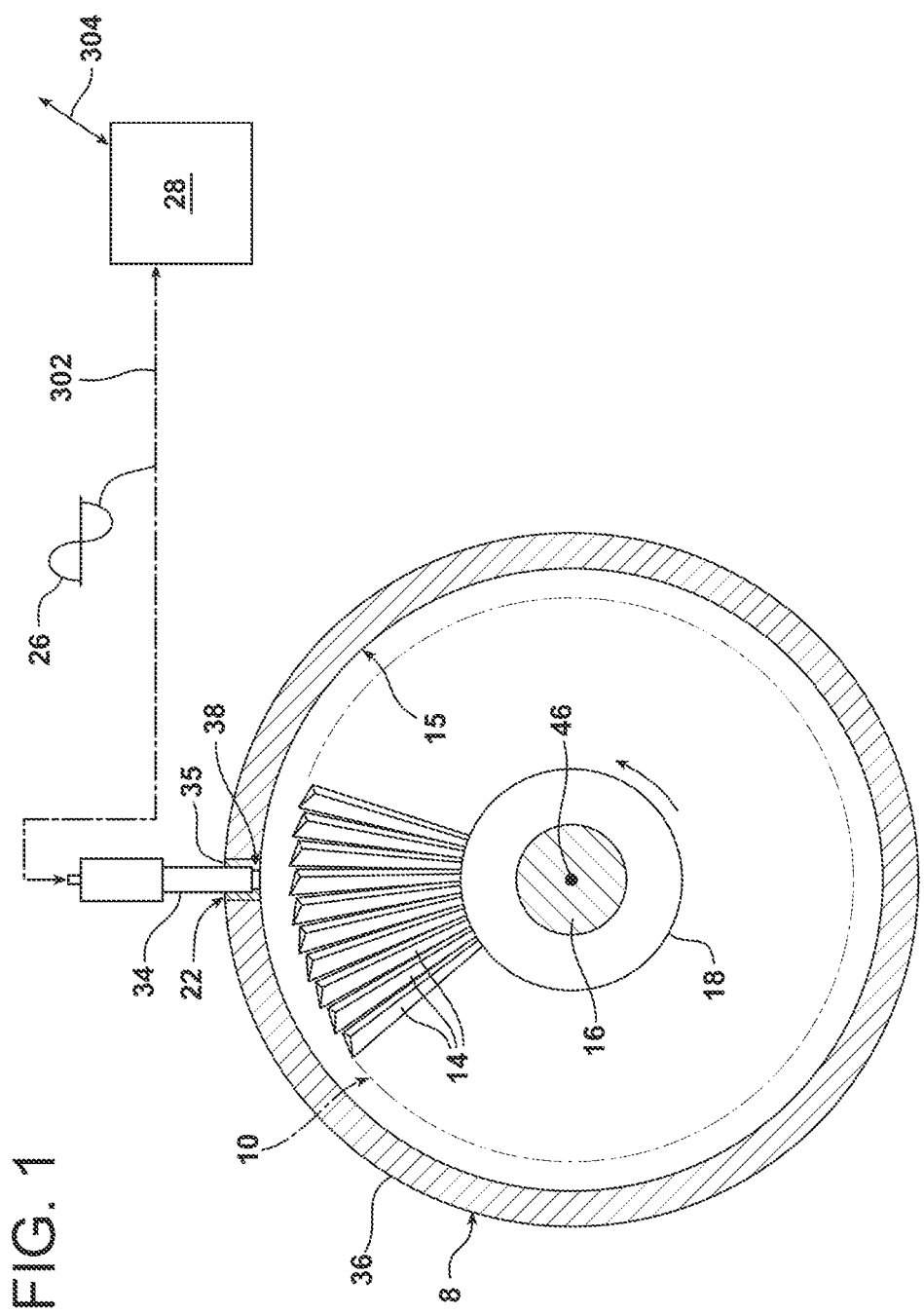

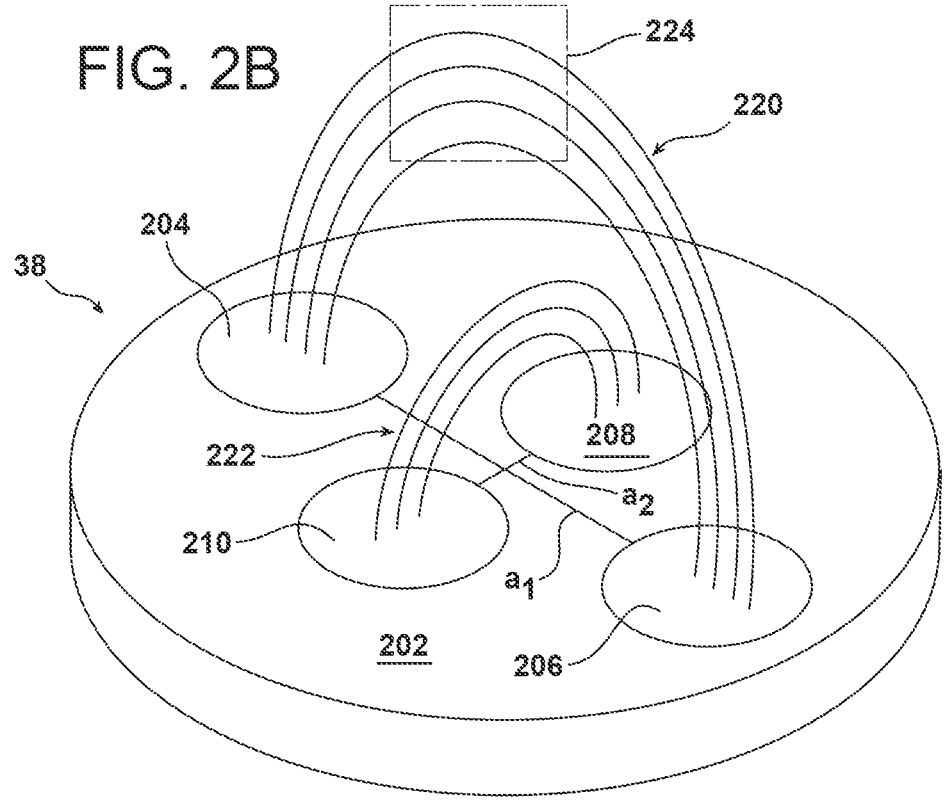
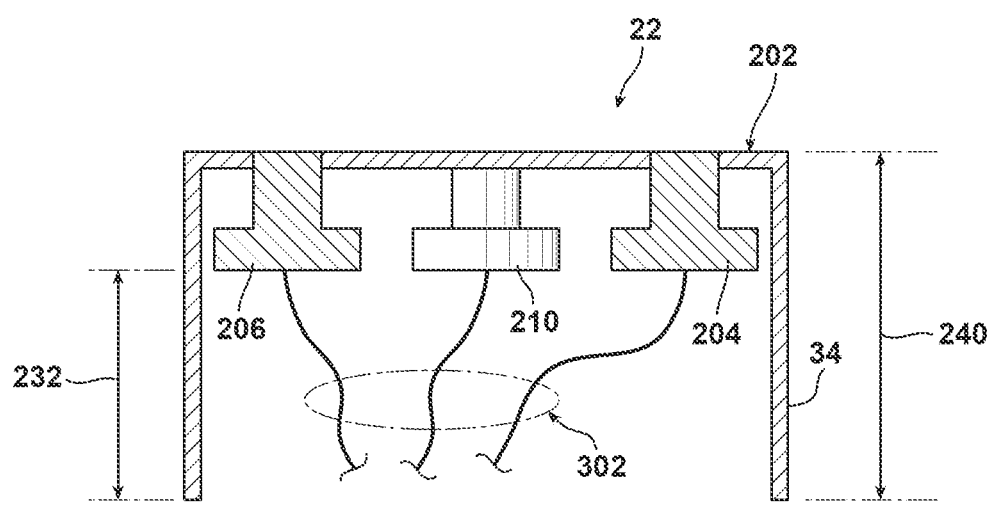

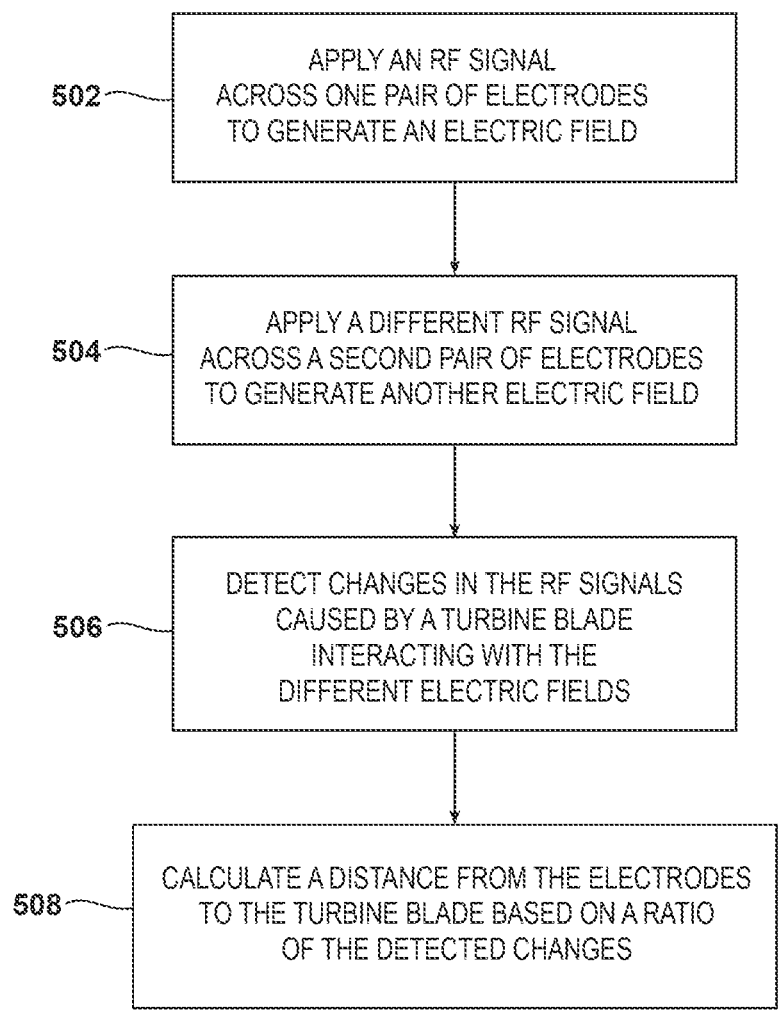

CAPACITIVE SENSOR WITH ORTHOGONAL FIELDS

FIELD OF THE INVENTION

The present invention relates to the field of non-contact sensors and, more particularly to a non-contact capacitive distance measurement sensor adapted for use in a turbine engine.

BACKGROUND OF THE INVENTION

A high speed turbo machine, such as, for example, a steam or gas turbine, generally comprises a plurality of blades arranged in axially oriented rows, the rows of blades being rotated in response to the force of a high pressure fluid flowing axially through the machine. It is common to monitor the position of the blades relative to a flowpath wall within the turbine, both during the design and testing of the turbine and during normal operation of the turbine. For example, it is known to use non-contacting proximity sensors or probes to detect a gap distance between the blade tips and the flowpath wall, as well as detect blade vibrations.

One conventional proximity sensor includes a capacitance gap sensor that has a single sensing electrode that is energized by a voltage so as to generate an electric field in the expected path of a turbine blade. The casing of the turbine provides a virtual ground for the electrode such that the electrode and the turbine casing act as a capacitor. When a turbine blade passes through the generated electric field, the capacitance between the electrode and the turbine casing changes as well. A change in the electrode's energizing voltage may be detected as a result of a change in the capacitance between the electrode and the virtual ground. The magnitude of the change in the energizing voltage is used as an indicator of a proximity of the turbine blade to the electrode.

The above approach has a number of drawbacks. The noise resulting from using the turbine casing as the virtual ground reduces the distance which the sensor can be separated from the circuitry which generates the energizing voltage and analyzes the results. Calibrating a detected change to a predetermined distance is difficult and is limited to a specific installation because the composition and the shape of the turbine blades have an effect on the magnitude at which an energizing voltage may change. Additionally, the ambient conditions where the sensor is located affects the magnitude of a resulting change in the sensor's capacitance. Furthermore, the conditions within a turbine, such as near the first and second row, may reach temperatures of about 1700 C or more. Operation in such an environment can degrade the performance of a conventional capacitance gap sensor such that it may fall out of calibration in a matter of days or weeks.

Accordingly, there is currently an unmet need for a proximity sensor, for example a turbine blade proximity sensor, which provides accurate results in a variety of environments, over a relatively long period of time without re-calibration.

SUMMARY OF THE INVENTION

One aspect of the present invention relates to a capacitive probe that includes a sensor body having an upper surface, and first, second, third and fourth electrodes on the sensor body upper surface. The first electrode has a top portion extending above the sensor body upper surface and a bottom portion, opposite the top portion, configured for electrical communication with a first electromagnetic signal. The second electrode has a top portion extending above the sensor body upper surface and a bottom portion, opposite the top portion, configured for electrical communication with the first electromagnetic signal, wherein the first and second electrodes are aligned along a first axis. The third electrode has a top portion extending above the sensor body upper surface and a bottom portion, opposite the top portion, configured for electrical communication with a second electromagnetic signal. The fourth electrode has a top portion extending above the sensor body upper surface and a bottom portion, opposite the top portion, configured for electrical communication with the second electromagnetic signal, wherein the third and fourth electrodes are aligned along a second axis substantially perpendicular to the first axis.

Another aspect of the present invention relates to a proximity sensor that comprises a first pair of electrodes aligned along a first axis and a second pair of electrodes aligned along a second axis substantially perpendicular to the first axis. The proximity sensor also includes a signal generator configured to apply a first signal across the first pair of electrodes to produce a first electric field and to apply a second signal across the second pair of electrodes to produce a second electric field. There is a detector configured to concurrently detect a first change in the first signal due to an object interacting with the first electric field and a second change in the second signal due to the object interacting with the second electric field. The proximity sensor further includes a comparator configured to determine a distance of the object from the first and second pair of electrodes based on a ratio of the first and second changes.

Yet another aspect of the present invention relates to a method for determining a distance from a probe to an object. The method includes generating a first electric field by applying a first signal across a first pair of electrodes aligned along a first axis and generating a second electric field by applying a second signal across a second pair of electrodes aligned along a second axis substantially perpendicular to the first axis. After generating the signals, the method includes concurrently detecting a first change in the first signal due to the object interacting with the first electric field and a second change in the second signal due to the object interacting with the second electric field. A distance of the object from the first and second pair of electrodes can be calculated based on a ratio of the first and second changes.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 1 is a diagrammatic view illustrating a turbine and a proximity sensor probe in accordance with the principles of the present invention;

FIG. 2A-FIG. 2C are different views of multi-electrode sensor in accordance with the principles of the present invention;

FIG. 5 is a flowchart of an exemplary method for calculating proximity of an object to a sensor in accordance with the principles of the present invention.

DETAILED DESCRIPTION OF THE INVENTION

Figure 2A:
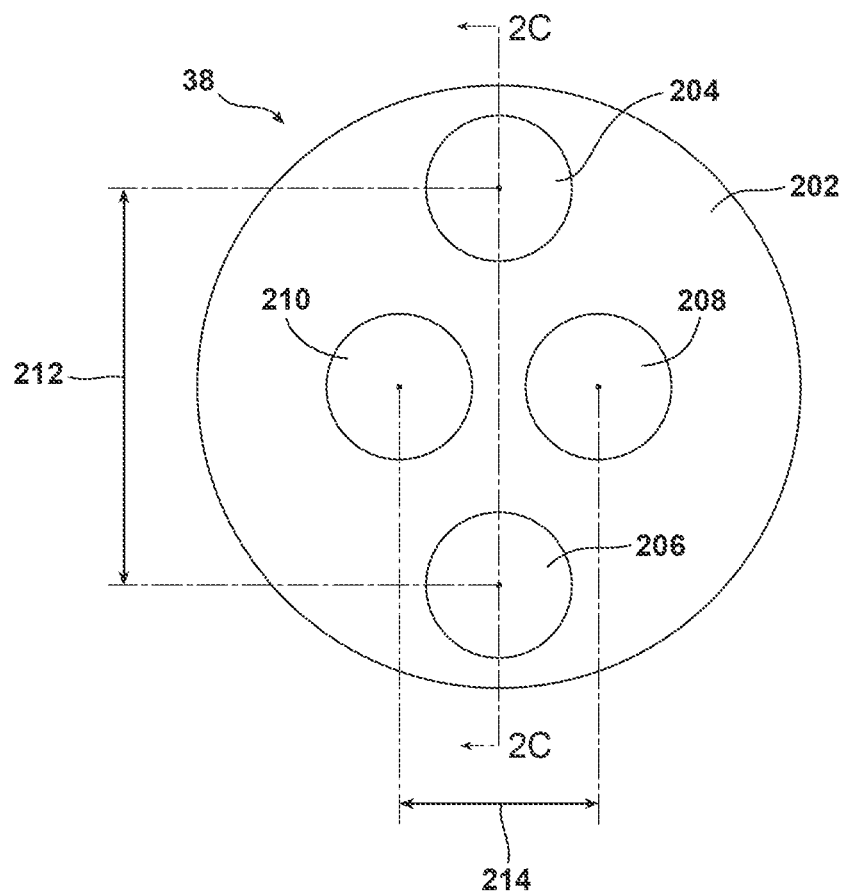

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

FIG. 1 diagrammatically illustrates a turbine 8 including a turbine blade row 10 in which the embodiments of the present invention can be employed in a proximity sensor for a blade proximity monitoring system. In addition, it should be understood that the proximity sensor described herein may be incorporated in other systems such as, for example, to measure a gap between a rotor and stationary vanes or casing. Turbine blades 14 are connected to a rotor 16 by means of a rotor disk 18 for rotation about a longitudinal axis 46 of the turbine 8. Outer ends of the turbine blades 14 are located near a circumferential outer shroud 15 defining a hot gas flowpath through the turbine 8.

A proximity sensor probe 22 in accordance with the principles of the present invention is also shown in FIG. 1. In the illustrated embodiment, one exemplary probe sensor 22 is shown. However, embodiments of the present invention also contemplate a plurality of individual probe sensor structures or probes in circumferentially spaced relation to each other for monitoring the proximity of the turbine blades 14 relative to the outer shroud 15.

Referring to FIG. 1, the probe 22 may comprise a probe shaft 34 for extending through an opening 35 of a casing or wall portion 36 of the turbine 8. The probe shaft 34 supports a sensor 38 near a tip of the turbine blades 14. For example, the sensor 38 may be spaced such that when a turbine blade 14 is at its closest location relative the sensor 38, they are spaced by about 1 mm.

The mounting of the probe sensor structure 22 through the wall portion 36 rigidly affixes the probe sensor structure 22, for example, within a through opening in the wall portion 36. As described below, a probe control module 28 produces a signal 26 that is applied to the sensor 38 through a communication medium 302 (e.g., shielded coaxial cable). As the blades 14 rotate about an axis 46, the proximity of the sensor 38 to one of the turbine blades 14 produces a change in the signal 26. The probe control module 28 can then be used to analyze the observed changes to signal 26 to determine a distance from the sensor 38 to a nearby turbine blade 14. As mentioned above, this proximity information can be communicated (e.g., via a communications channel 304) to a proximity monitoring system, a vibration monitoring system or other monitoring systems.

FIG. 2A is a top view of a sensor 38 in accordance with the principles of the present invention. The sensor 38 includes a top surface 202 on which four different electrodes 204, 206, 208, 210 are located. In particular, each of the electrodes 204, 206, 208, 210 includes a respective portion that extends above the top surface 202. The relative positional terms "top", "above", etc. are merely used for convenience when referring to and describing the content of the various figures provided herein. However, one of ordinary skill will recognize that the sensor 38 of FIG. 2A-FIG. 2C may be oriented in other configurations than those depicted; thus the terms "top", "bottom", "above", "below", etc. are not intended to limit the scope of the present invention to only those specific orientations of the sensor 38 and the probe 22.

The electrodes 204, 206, 208, 210 can each be constructed of similar material and have a similar shape (e.g., circular). In particular, the material of the sensor 204, 206, 208, 210 can be selected so as to provide a desired electrical field (as discussed below) but also be able to withstand the temperatures and pressures commonly experienced within a high-temperature region of a turbine such as, for example, near the first and second rows of the turbine. Electrodes comprising various combinations of platinum and Inconel may, for example, be used. As for size, the diameter of each of the electrodes 204, 206, 208, 210 may, for example, be about 6 mm±1 mm.

Referring to FIGS. 2A and 2B, the pair of electrodes 204, 206 is aligned along a first axis $a_1$ and their centers are separated by a first distance depicted as the line 212. The direction of this first axis $a_1$ is parallel with the line 212. The pair of electrodes 208, 210 is aligned along a second axis $a_2$ and their centers are separated by a second distance depicted as the line 214. The direction of this second axis $a_2$ is parallel with the line 214. The electrodes 204, 206, 208, 210 are positioned on the top surface 202 such that the first axis $a_1$ and the second axis $a_2$ are substantially orthogonal, i.e., perpendicular, to one another, within a tolerance of a few degrees. Additionally, the first distance 212 may be different than the second distance 214. In a particular embodiment, the distances have a 2:1 ratio such that the first distance 212 is about 18 mm and the second distance 214 is about 9 mm. An exemplary diameter for the top surface 202 of the sensor 38 is about 25 mm.

As described in more detail below, a first electromagnetic signal can be applied across two electrodes 204, 206 while a second electromagnetic signal can be applied across the other two electrodes 208, 210. As a result, a first electric field 220 (FIG. 2B) is produced that couples the two electrodes 204, 206 and a second electric field 222 (FIG. 2B) is produced that couples the other two electrodes 208, 210. The electric fields 220, 222 have portions that extend outwardly from the top surface 202. Although not shown in FIG. 2B, respective portions of the respective electric fields 220, 222 exist in a region 224 above the top surface 202 at which it is expected that a turbine blade will pass when the sensor 38 is installed in a turbine system as a proximity sensor.

Because of the orientation and alignment of the electrodes 204, 206, 208, 210, the electric field 220 is aligned in a direction that is substantially orthogonal to the electric field 222. Thus, the region 224 will be occupied by a portion of the electric field 220 and a portion of the other, orthogonally-oriented electric field 222. A turbine blade passing through the region 224 will interact with the two electric fields 220, 222.

FIG. 2C depicts a side view of the sensor 38 that shows one exemplary structure for the electrodes 204, 206, 208, 210. As shown, each of the electrodes (e.g., 204) can resemble an upside-down table having a shaft extending away from the top surface 202. Guard or insulating regions (not shown) may be included between electrodes to reduce the coupling between pairs of electrodes except for electric field lines that extend outward toward region 224. The shaft 34 of the probe 22 can form a flange extending away from the top surface 202 for a distance 240 of about 33 mm, for example, and extend below the bottom of the electrodes 204, 206, 208, 210, by a distance 232 of about 25 mm.

As shown in FIG. 2C, each of the electrodes 204, 206, 208, 210, have a portion below the top surface 202 that is in electrical communication with the communication medium 302 that is providing the electromagnetic signals for the electrodes 204, 206, 208, 210. The details of one exemplary coupling of electrodes 204, 206, 208, 210 with the communication medium 302 is provided with respect to FIG. 3.

Figure 3:
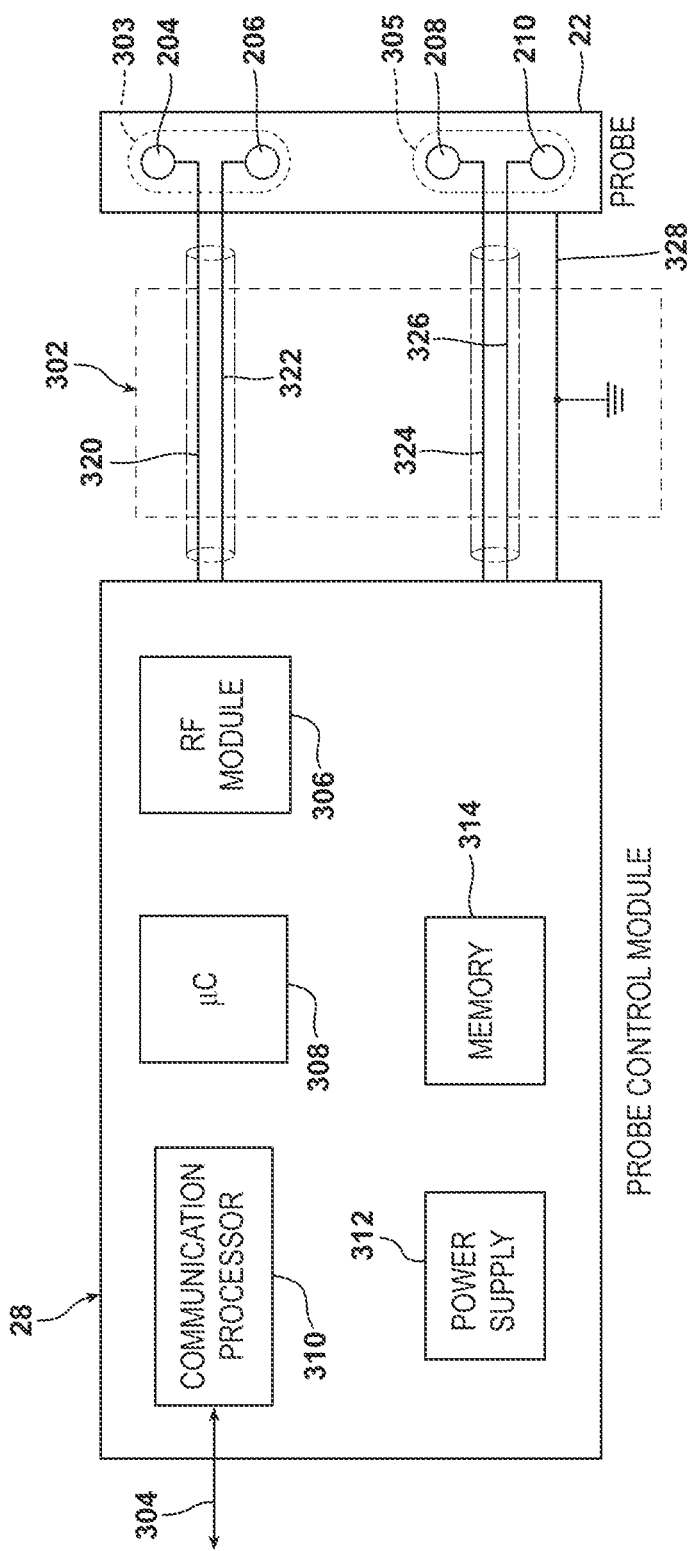
FIG. 3 is a block diagram illustrating the functional elements of a probe control module in accordance with the principles of the present invention.

FIG. 3 is a block diagram illustrating the functional elements of a probe control module 28 in accordance with the principles of the present invention. The probe 22 and the electrodes 204, 206, 208, 210 are shown schematically in FIG. 3. However, the actual configuration, positions, alignment, and functionality of the electrodes 204, 206, 208, 210 continue to be as discussed with respect to the sensor 38 of FIG. 2A-FIG. 2C.

In particular, the communication medium 302 may include a first coaxial cable with a first conductor 320 coupled with the first electrode 204 and a second conductor 322 coupled with the second electrode 206. This first coaxial cable provides a first electromagnetic signal to the first pair of electrodes 204, 206. The communication medium 302 also includes a second coaxial cable. The second coaxial cable includes a first conductor 324 coupled with the third electrode 208 and a second conductor 326 coupled with the fourth electrode 210. This second coaxial cable provides a second electromagnetic signal to the second pair of electrodes 208, 210. Each of the first and second coaxial cables can also include a respective ground conductor that can directly tie the probe 22 and the probe control module 28 to a common ground 328.

By applying the first electromagnetic signal to the first pair of electrodes 204, 206 the electrodes 204, 206 are capacitively coupled to one another by the resulting electric field 220. Thus, the coupled electrodes 204, 206 behave as a capacitor 303 having a capacitance which varies based on the degree of coupling between the two electrodes 204, 206. By applying the second electromagnetic signal to the second pair of electrodes 208, 210 the electrodes 208, 210 are capacitively coupled to one another by the resulting electric field 222. Thus, the coupled electrodes 208, 210 behave as a capacitor 305 having a capacitance which varies based on the degree of coupling between the two electrodes 208, 210. Accordingly, a length of the first and second coaxial cables can be in the range of hundreds of meters so that the probe control module 28 may be located relatively distant from the probe 22.

The probe control module 28 includes an RF module 306 that can generate and analyze the first and second electromagnetic signals that are applied to the electrodes 204, 206, 208, 210 using the communication medium 302. The RF module 306 may also be configured to determine a proximity of a turbine blade based on a state or condition of the electromagnetic signal.

There is a microcontroller 308 or other programmable processor, or equivalent, which controls the operation of the various components of the probe control module 28. One such component is a communication processor 310 that can communicate with other systems (e.g., a proximity monitoring system) via a communications channel 304. In this manner, the probe control module 28 can determine turbine blade proximity information and communicate that information to a proximity monitoring system or other monitoring systems. A memory 314 can store data that, for example, includes instructions that affect how the microcontroller 308 operates, calibration information relating detected signals to distance information, configuration variables for the probe and electrodes, and historical measurement information. A power supply 312 may be provided that supplies appropriate power to the various components.

Figure 4:
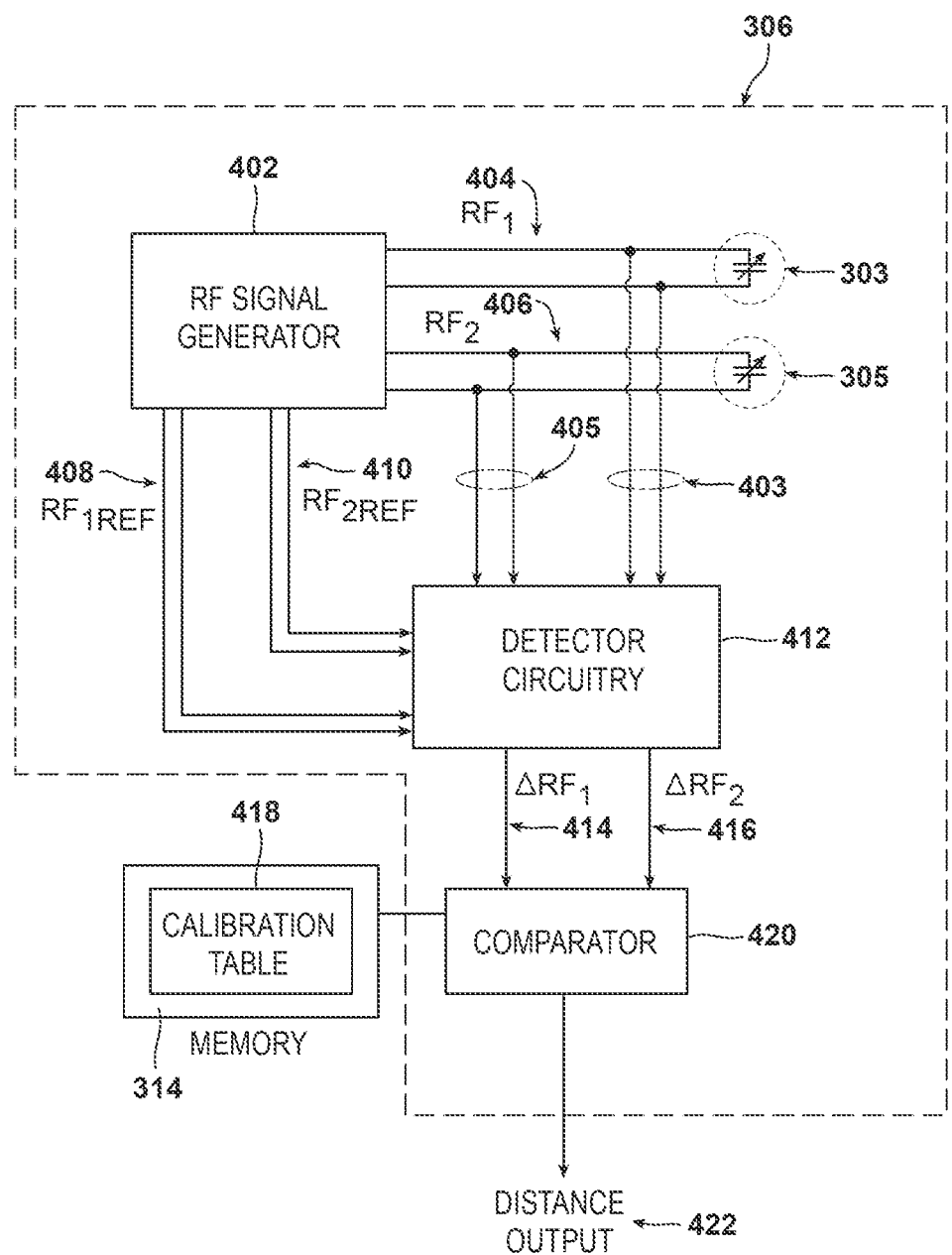
FIG. 4 is a block diagram showing more details of the probe control module of FIG. 3.

FIG. 4 is a block diagram showing more details of the probe control module 28 of FIG. 3. In particular, various sub-components of the RF module 306 are depicted. The depiction of sub-components as separate blocks in FIG. 4, is not intended to require that separate hardware or circuitry must necessarily be used to perform the activities of the respective components. Instead, FIG. 4 provides a conceptual diagram of different functions performed by the RF module 306.

The RF module 306 includes a signal generator 402 that produces a first electromagnetic signal $RF_1$ 404 and a second electromagnetic signal $RF_2$ 406. The signals $RF_1$ and $RF_2$ can both be sinusoidal signals having a respective frequency in the range of 1-100 MHz and have a power level from 0 to 25 dBm depending on a required operating range. As an alternative to sinusoidal signals, waveforms which are square waves or saw-tooth waves may provide beneficial results as well. Even though both signals $RF_1$ and $RF_2$ may have respective frequencies within a same general band, embodiments of the present invention contemplate that the frequency of the signal $RF_1$ does not equal the frequency of the signal $RF_2$. As mentioned above, the first electromagnetic signal $RF_1$ 404 may be applied to the first pair of electrodes 204, 206 so as to probe a capacitor 303 with variable capacitance. Also, the second electromagnetic signal $RF_2$ 406 may be applied to the second pair of electrodes 208, 210 so as to probe another capacitor 305 with its own variable capacitance.

Detector circuitry 412 is coupled across the capacitors 303, 305 to detect changes in the electromagnetics signals $RF_1$, $RF_2$ based on changes in the respective capacitances of the capacitors 303, 305. Such capacitance changes may be the result of a turbine blade interacting with the respective fields 220, 222 that are coupling the electrodes 204, 206, 208, 210. In particular, the detector circuitry 412 may have a first connection 403 with the first electromagnetic signal $RF_1$ 404 and a second connection 405 with the second electromagnetic signal $RF_2$ 406.

The first electromagnetic signal $RF_1$ 404 has a number of attributes or properties that describe its waveform during a particular time period. For instance the first signal 404 has an amplitude, a frequency, and a phase. These attributes of the first electromagnetic signal $RF_1$ 404 are influenced by a capacitance value of the capacitor 303. Thus, if a capacitance of the capacitor 303 changes from an initial value to a subsequent value, then the amplitude of the first signal 404 will change from an initial amplitude to a subsequent amplitude. Similarly, the frequency of the first signal 404 and the phase of the first signal 404 will also change, respectively, from an initial value to a subsequent value. A similar phenomenon occurs for the second signal 406 and the capacitor 305. However, because of the different spacing between the electrode pair 204, 206 and electrode pair 208, 210, the relative capacitance values of the capacitor 303 and the capacitor 305 may vary. Accordingly, the changes from an initial to a subsequent second signal 406 may not necessarily have the same absolute magnitude as the changes described above with respect to the first signal 404.

Conceptually, then, the RF signal generator 402 produces a first reference signal $RF_{1ref}$ 408 and a second reference signal $RF_{2ref}$ 410. The first reference signal 408 may represent a signal having an amplitude, frequency, and phase for $RF_1$ when the electric field 220 between the electrode pair 204, 206 has no portion of a turbine blade interacting with the electric field 220. As a turbine blade interacts with the electric field 220, the detector circuitry 412 can detect corresponding amplitude, frequency, and phase of the first electromagnetic signal $RF_1$ 404 as it is being affected by the capacitor 303 formed from the electrode pair 204, 206. The detector circuitry 412 can, thus, determine a change in the amplitude, frequency, and phase of the first signal 404 as compared with the first reference signal 408.

The second reference signal 410 may represent a signal having an amplitude, frequency, and phase for $RF_2$ when the electric field 222 between the electrode pair 208, 210 has no portion of a turbine blade interacting with the electric field 222. As a turbine blade interacts with the electric field 222, the detector circuitry 412 can detect corresponding amplitude, frequency, and phase of the second electromagnetic signal $RF_2$ 406 as it is being affected by the capacitor 305 formed from the electrode pair 208, 210. The detector circuitry 412 can, thus, determine a change in the amplitude, frequency, and phase of the second signal 406 as compared with the second reference signal 410.

While changes in any of the waveform attributes (e.g., amplitude, frequency, phase) may be detected by the detector circuitry 412, using only one of the attributes is generally sufficient to accurately determine the proximity of a turbine blade in accordance with the principles of the present invention. Thus, the detector circuitry 412 may determine a change $\Delta RF_1$ 414 between the frequency (for example) of the first signal $RF_1$ and the first reference signal $RF_{1ref}$. Also, the detector circuitry 412 may determine a change $\Delta RF_2$ 416 between the frequency (for example) of the second signal $RF_2$ and the second reference signal $RF_{2ref}$.

A comparator 420 can then determine a value, r, equal to the ratio of $\Delta RF_1 : \Delta RF_2$. One of ordinary skill will recognize that the ratio $\Delta RF_2 : \Delta RF_1$ may be used as well without departing from the scope of the present invention. As part of the development of the probe 22 and the sensor 38, calibration steps were performed to relate a distance of an object, d, to a particular value of r. In other words, a function, f(r), was developed such that the f(r)=d. One of ordinary skill will recognize that depending on the calibration test data, the function f(r) may be a linear, quadratic, or some other polynomial function of r. Regardless of the exact nature of the function f(r), a calibration table 418 can be generated and stored within the memory 314 of the probe control module 28. Utilizing such a table, the comparator 420 can easily determine and output a distance 422 from an object to the sensor 38 based on the ratio of the detected changes $\Delta RF_1$ 414 and $\Delta RF_2$ 416.

FIG. 5 is a flowchart of an exemplary method for calculating proximity of an object to a sensor in accordance with the principles of the present invention such as by using, for example, the circuitry and sensors of FIG. 2A, FIG. 2B, FIG. 2C, FIG. 3, and FIG. 4. In step 502, an electromagnetic signal, such as in the RF range of 10-100 MHz, may be applied across a first pair of electrodes to generate an electric field coupling those electrodes.

Concurrently, in step 504, a different electromagnetic signal can be applied across a second pair of electrodes to generate another electric field coupling the second pair of electrodes. The first and second pairs of electrodes are part of a proximity sensor and are arranged in such a manner that portions of their respective electric fields both concurrently occupy a region of space distant from the electrodes.

When an object also occupies that region of space it will interact with each of the electric fields and cause a respective change in each of the electromagnetic signals. Because the first pair of electrodes may be separated by a distance different than a distance that separates the second pair of electrodes, the respective change caused by the object on each of the electromagnetic signals may differ. Also, because the electromagnetic signals, themselves, are different, the respective change caused by the object on each of the electromagnetic signals may differ. Regardless, in step 506, a respective change is detected in each of the electromagnetic signals caused by an object interacting with the different electric fields.

In the example, where determining the distance to a turbine blade is desired, the rate at which the changes are sampled can vary. When a turbine is operating in a steady-state condition and an average blade distance is monitored, then determining a change to the electromagnetic signals can occur every 10 to 30 seconds. However, during a turbine start-up or other transient condition and for individual blade distance measurement, the changes to the electromagnetic signals can be detected at a rate of 10 MHz or higher.

In step 508, a ratio of the respective changes can be calculated. Using previously determined calibration data, the calculated ratio can then be used to identify an object distance corresponding to that calculated ratio. Thus, the method of FIG. 5 determines a distance from an object to a sensor based on a ratio of changes to two different electric fields caused by that object interacting with the electric fields, instead of determining the distance based on an absolute change to a single electric field. As the electrodes degrade because of environment, age, and other conditions, the changes to the electrodes used to generate the different electric fields will cause changes in the electric fields that are generated and the respective electromagnetic signals related to those fields. However, despite this degradation of electrodes and the resulting changes, the ratio of the changes to the electromagnetic signals caused by an interacting object will not change dramatically and will still substantially correspond with the calibration data used to determine distance between the sensor and an object.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A proximity sensor comprising:
   a first pair of electrodes aligned along a first axis;
   a second pair of electrodes aligned along a second axis substantially perpendicular to the first axis;
   a signal generator configured to apply a first signal across the first pair of electrodes to produce a first electric field and to apply a second signal across the second pair of electrodes to produce a second electric field that is substantially perpendicular to the first electric field, wherein the first and second electric fields are produced concurrently;
   a detector configured to concurrently detect a first change in the first signal due to an object interacting with the first electric field and a second change in the second signal due to the object interacting with the second electric field; and
   a comparator configured to determine a distance of the object from the first and second pair of electrodes based on a ratio of the first and second changes.

2. The proximity sensor of claim 1, wherein:
   the first pair of electrodes are separated along the first axis by a first distance; and
   the second pair of electrodes are separated along the second axis by a second distance different than the first distance.

3. The proximity sensor of claim 2, wherein the first distance is about twice as much as the second distance.

4. The proximity sensor of claim 1, wherein the first signal is a radio frequency signal having a first frequency and the second signal is a radio frequency signal having a second frequency different than the first frequency.

5. The proximity sensor of claim 4, wherein each of the first and second frequencies are between about 1 MHz and 100 MHz.

6. The proximity sensor of claim 1, wherein the first change relates to a change in amplitude of the first signal and the second change relates to a change in amplitude of the second signal.

7. The proximity sensor of claim 1, wherein the first change relates to a change in phase of the first signal and the second change relates to a change in phase of the second signal.

8. The proximity sensor of claim 1, wherein the first change relates to a change in frequency of the first signal and the second change relates to a change in frequency of the second signal.

9. The proximity sensor of claim 1, wherein the first and second pairs of electrodes are attached to a probe configured to be located within a high temperature region of a gas turbine engine.

10. A method for determining a distance from a probe to an object, comprising:
generating a first electric field by applying a first signal across a first pair of electrodes aligned along a first axis;
generating, concurrently with the first electric field, a second electric field by applying a second signal across a second pair of electrodes aligned along a second axis substantially perpendicular to the first axis, wherein the first electric field is substantially perpendicular to the second electric field;
concurrently detecting a first change in the first signal due to the object interacting with the first electric field and a second change in the second signal due to the object interacting with the second electric field; and
calculating a distance of the object from the first and second pair of electrodes based on a ratio of the first and second changes.

11. The method of claim 10, wherein:
the first pair of electrodes are separated along the first axis by a first distance; and
the second pair of electrodes are separated along the second axis by a second distance different than the first distance.

12. The method of claim 11, wherein the first distance is about twice as much as the second distance.

13. The method of claim 10, wherein the first signal is a radio frequency signal having a first frequency and the second signal is a radio frequency signal having a second frequency different than the first frequency.

14. The method of claim 13, wherein each of the first and second frequencies are between about 1 MHz and 100 MHz.

15. The method of claim 10, wherein the first change relates to a change in amplitude of the first signal and the second change relates to a change in amplitude of the second signal.

16. The method of claim 10, wherein the first change relates to a change in phase of the first signal and the second change relates to a change in phase of the second signal.

17. The method of claim 10, wherein the first change relates to a change in frequency of the first signal and the second change relates to a change in frequency of the second signal.

18. The method of claim 10, comprising:
positioning the probe within a high temperature region of a gas turbine engine, and wherein the object is a rotating blade of the gas turbine engine.

19. A capacitive probe comprising:
a sensor body upper surface;
a first electrode located on the sensor body upper surface, the first electrode having a first top portion extending above the sensor body upper surface and a first bottom portion, opposite the first top portion, configured for electrical communication with a first electromagnetic signal;
a second electrode located on the sensor body upper surface, the second electrode having a second top portion extending above the sensor body upper surface and a second bottom portion, opposite the second top portion, configured for electrical communication with the first electromagnetic signal, wherein the first and second electrodes are aligned along a first axis;
a third electrode located on the sensor body upper surface, the third electrode having a third top portion extending above the sensor body upper surface and a third bottom portion, opposite the third top portion, configured for electrical communication with a second electromagnetic signal; and
a fourth electrode located on the sensor body upper surface, the fourth electrode having a fourth top portion extending above the sensor body upper surface and a fourth bottom portion, opposite the fourth top portion, configured for electrical communication with the second electromagnetic signal, wherein the third and fourth electrodes are aligned along a second axis substantially perpendicular to the first axis.

20. The capacitive probe of claim 19, wherein:
the first and second electrodes are separated by a first distance along the first axis; and
the third and fourth electrodes are separated by a second distance along the second axis, wherein the second distance is substantially twice the first distance.

* * * * *